United States Patent [19]

Bonse et al.

[11] 4,279,921
[45] Jul. 21, 1981

[54] DICHLOROMALEIC ACID DIAMIDE DERIVATIVES AND THEIR USE AS FUNGICIDES

[75] Inventors: Gerhard Bonse, Cologne; Heinz U. Blank, Odenthal; Wilhelm Brandes, Leichlingen; Volker Paul, Solingen, all of Fed. Rep. of Germany

[73] Assignee: Bayer Aktiengesellschaft, Leverkusen, Fed. Rep. of Germany

[21] Appl. No.: 123,868

[22] Filed: Feb. 22, 1980

Related U.S. Application Data

[62] Division of Ser. No. 8,145, Jan. 31, 1979.

[30] Foreign Application Priority Data

Feb. 23, 1978 [DE] Fed. Rep. of Germany ....... 2807662

[51] Int. Cl.³ .................... A01N 43/08; A01N 43/16; C07D 307/54; C07D 309/32
[52] U.S. Cl. .............................. 424/285; 260/347.3; 260/345.7 R; 424/275
[58] Field of Search ................ 260/347.3, 345.7 R; 424/275, 285

[56] References Cited

PUBLICATIONS

Leder, J. Prakt. Chem., vol. 130 (1931) p. 255.

*Primary Examiner*—Richard Raymond

*Attorney, Agent, or Firm*—Sprung, Felfe, Horn, Lynch & Kramer

[57] ABSTRACT

The present invention relates to dichloromaleic acid diamides of the formula

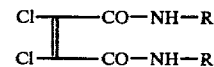

in which R represents an optionally substituted aliphatic radical with up to 8 carbon atoms, a cycloalkyl radical with 3 to 6 carbon atoms or a substituted phenyl radical which possess fungicidal properties and are produced by reacting a dichloromaleic acid halide of the formula

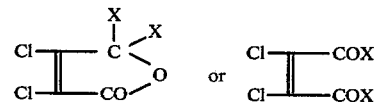

in which X is halogen with an amine of the formula $H_2N-R$ in a diluent and in the presence of an acid-binding agent.

5 Claims, No Drawings

DICHLOROMALEIC ACID DIAMIDE DERIVATIVES AND THEIR USE AS FUNGICIDES

This is a division of application serial No. 008,145, filed Jan. 31, 1979 now pending.

The present invention relates to and has for its objects the provision of particular new dichloromaleic acid diamides which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

It has already been disclosed that N-(p-fluorophenyl)-2,3-dichloromaleimide has a very good action against citrus scab (see, for example, DT-OS (German Published Specification) No. 2,156,967 and U.S. Pat. No. 3,734,927). However, the spectrum of action of the compound mentioned is not completely satisfactory when low amounts are applied. Furthermore, zinc ethylene-1,2-bis-dithiocarbamidate has been generally known for a long time as a standard preparation with a fungicidal action (R. Wegler, "Chemie der Pflanzenschutz- und Schädlingsbekämpfungsmittel" ("Chemistry of plant protection agents and agents for combating pests"), Springer-Verlag, Berlin/Heidelberg/New York (1970), volume 2, page 65).

Moreover, it has been known for a relatively long time that when aniline is acylated with dichloromaleic acid dichloride, a product mixture is formed (see, in this context, J. prakt. Chemie 130, 255 (1931)). Even though, as has also become known recently, the dichloromaleic acid dichloride exists exclusively in the lactoidal (cyclic) form as tetrachloro-5H-furan-2-one, reactions of lactoidal acid chlorides of dicarboxylic acids with nucleophilic reactants can in principle lead to products which contain an intact lactoidal ring (Chem. Ber. 104, 3,378 (1971)), or can give open-chain derivatives, the ring being opened (Chem. Ber. 109, 1,163 (1976)). Accordingly, in the literature (J. prakt. Chem. 130, 255 (1931)), a product mixture is in each case described when aniline is acylated with dichloromaleic acid dichloride, and in particular a yellow product with a melting point of 170° C. and a white product with a melting point of 193° C., both products having the same empirical formula $C_{16}H_{12}Cl_2N_2O_2$. Formation of solely the white product (melting point 193° C.), which is described as symmetric dichlormaleic acid bis-phenylamide, was only possible if the dichloromaleic acid dichloride had first been subjected to a treatment with aluminum chloride, which was explained as conversion of the lactoidal form into the open-chain symmetric form.

No biological actions have hitherto been disclosed for the above-mentioned, previously described dichloromaleic acid bis-phenylamide (J. prakt. Chem. 130, 255 (1931).

The present invention now provides, as new compounds, the dichloromaleic acid diamide derivatives of the general formula

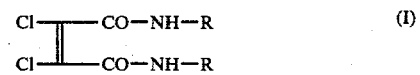

in which

R represents an optionally substituted aliphatic radical with up to 8 carbon atoms, a cycloalkyl radical with 3 to 6 carbon atoms or a substituted phenyl radical.

Preferably, R represents a straight-chain or branched, saturated or unsaturated aliphatic radical with up to 6 carbon atoms, which can optionally carry one or more substituents selected from halogen atoma, cyano, $C_1$-$C_4$ alkoxy, $C_1$-$C_4$ alkylthio, phenyl, phenoxy, a heterocyclic group which contains 5 or 6 ring members, which can be saturated or unsaturated and which contains one or more hetero-atoms selected from oxygen atoms, sulphur atoms and nitrogen atoms (examples which may be mentioned are the furyl group, the pyranyl group (derivatives or pyrane) and hydrogenated and partially hydrogenated derivatives thereof), and the amino group, each hydrogen atom of which optionally can be replaced by alkyl with up to 4 carbon atoms or by phenyl; or represents a cycloalkyl group with 5 or 6 carbon atoms; or represents phenyl that is carrying one or more substituents each selected independently from alkyl, alkenyl, alkynyl, alkoxy and alkylthio with up to 3 carbon atoms in each case, phenyl, phenoxy, halogen, nitro, cyano, halogenomethyl (for example trifluoromethyl), halogenoethyl, trifluoromethoxy, trifluoromethylthio, thiocyanato, carboxyl groups and alkoxycarbonyl groups with up to 4 carbon atoms in the alkyl part, and the acetylamino group.

Surprisingly, the dichloromaleic acid diamide derivatives of the formula (I) according to the invention exhibit a considerably more powerful fungicidal action than the compounds known from the state of the art. The substances according to the invention thus represent an enrichment of the art.

The invention also provides a process for the production of a dichloromaleic acid diamide derivative of the formula (I), in which a dichloromaleic acid halide of the general formula

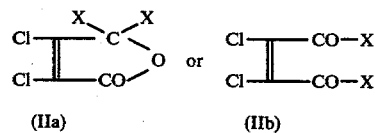

in which

X represents halogen, preferably chlorine, is reacted with an amine of the general formula $$H_2N-R \qquad (III),$$

in which

R has the meaning stated above, in a diluent and in the presence of an acid-binding agent.

Finally, as has also been found, a course of reaction leading solely to the open-chain symmetric compounds of the general formula (I) (even when compounds of the lactoidal type IIa are used as starting materials), can easily be effected by initially introducing into the reaction vessel the amine of the formula (III) to be acylated and then adding the dichloromaleic acid halide (formula IIa or IIb).

Furthermore, it is surprising that the formation of the single products of the formula (I) is achieved in a simple manner by the addition sequence according to the invention. The omission of the treatment of the dichloromaleic acid halide with aluminum chloride or another Lewis acid, which was necessary according to previous knowledge, denotes a simplification of the art.

If tetrachloro-5H-furan-2-one ("dichloromaleic acid dichloride") and ethylamine are used as starting materials, the course of the reaction can be represented by the equation which follows:

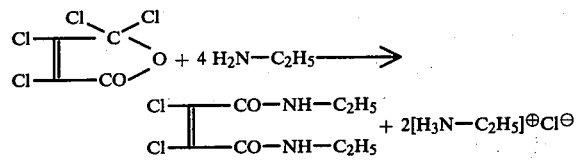

The dichloromaleic acid halides of the formula (II) are known and can be prepared by processes which are generally known, for example by halogenating dichloromaleic acid anhydride, for example either by using phosphorus pentachloride, phosgene or thionylchloride, or by using halogen, such as chlorine, in the presence of a catalyst, such as, for example, an iron salt.

The amines of the formula (III) are known compounds which are obtainable in a generally known manner and are customary in organic chemical laboratories. Thus, for example, [tetrahydropyran-2-yl]-methylamine, also called 2-aminomethyl-tetrahydropyrane, is obtained by hydrogenating 2-cyano-tetrahydropyrane, for example with lithium alanate or with hydrogen under pressure (see Beilstein 18, E ⅔, page 7,045). On the other hand, 2-aminomethyl-3,4-dihydropyrane can be prepared by hydrogenating 2-formyl-3,4-dihydropyrane under pressure, in the presence of ammonia.

The amines can, of course, also be used in the form of their acid-addition products, for example in the form of their hydrochlorides or hydrobromides, or in the form of adducts with organic acids, fumaric acid being mentioned as an example here.

Diluents which can be used for the reaction according to the invention are all the customary polar solvents. Water is preferably used, and also alcohols, for example methanol, ethanol or propanol, as well as ketones, such as acetone. Moreover, mixtures of different solvents can also be used, for example mixtures consisting of water and a water-miscible solvent.

Any of the customary acid-binding agents (bases) can be used as auxiliaries, especially inorganic acid-binding agents, such as alkali metal hydroxides and alkali metal carbonates, for example sodium hydroxide and potassium carbonate. If the reaction is carried out in an organic solvent, a tertiary amine is preferably used, for example triethylamine or pyridine.

Preferably, the amine of the formula (III) to be used as the starting material can also be used in excess and can thus simultaneously function as a reactant and as the acid-binding agent.

The reaction temperatures can be varied within a substantial range. In general, the reaction is carried out at about $-5°$ to $+150°$ C., preferably about $+10°$ to $50°$ C.

In carrying out the process according to the invention, 2 moles of the amine of the formula (III) and at least 2 moles of an acid-binding agent are preferably employed per mole of dichloromaleic acid dihalide of the formula (IIa) or (IIb), it also being possible, as already mentioned, to use the amine of the formula (III) in excess instead of a separate acid-binding agent; in the latter case, at least 4 moles of amine are then required per mole of dichloromaleic acid dihalide. The mixture is worked up in the usual manner, for example by a procedure in which the end product, which has precipitated from water, is filtered off and dried.

The active compounds according to the invention exhibit a powerful fungitoxic action. They do not damage crop plants in the concentrations required for combating fungi. For these reasons, they are suitable for use as plant protection agents for combating fungi. Fungitoxic agents are employed in plant protection for combating Plasmodiophoromycetes, Oomycetes, Chytridiomycetes, Zygomycetes, Ascomycetes, Basidiomycetes and Deuteromycetes.

The active compounds according to the invention have a broad spectrum of action and can be used against parasitic fungi which attack above-ground parts of plants or which attack the plants through the soil, as well as against seed-borne pathogens.

Thus they exhibit a particularly good activity against the causative organism of blight and brown rot of tomatoes (*Phytophthora infestans*) and the fungus *Pyricularia oryzae*, which causes a disease in rice.

In the cultivation of cereals, the active compounds have a good activity against cereal rust (*Puccinia recondita*), bunt of wheat (*Tilletia caries*) and stripe disease of barley (*Helminthosporium gramineum*).

As plant protection agents, the compounds according to the invention can be used for the treatment of soil, for the treatment of seed and for the treatment of above-ground parts of plants.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations as a mixture with other active compounds, such as fungicides, insecticides, acaricides, nematicides, herbicides, bird repellents, growth factors, plant nutrients and agents for improving soil structure.

The active compounds can be used as such, as their formulations or as the use forms prepared therefrom by further dilution, such as ready-to-use solutions, emulsions, suspensions, powders, pastes and granules. They may be used in the customary manner, for example by watering, spraying, atomizing, dusting, scattering, dry dressing, moist dressing, wet dressing, slurry dressing or encrusting.

Especially when used as leaf fungicides and leaf bactericides, the active compound concentrations in the use forms can be varied within a substantial range. They are, in general, from 0.5 to 0.0005% by weight, preferably from 0.2 to 0.001%.

In the treatment of seed, amounts of active compound of 0.01 to 50 g, especially 0.5 to 5 g, are generally employed per kilogram of seed.

For the treatment of soil, amounts of active compound of 1 to 1,000 g, preferably 10 to 200 g, are generally employed per cubic meter of soil.

In addition to the fungicidal action, the compounds according to the invention also exhibit, when applied in the appropriate amounts and concentrations, an action as plant growth regulators.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the novel compounds is shown in the following illustrative examples:

EXAMPLE 1

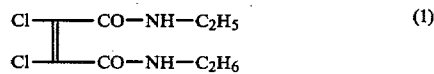

10.0 g (45.1 mmoles) of tetrachloro-5-furan-2-one ("dichloromaleic acid dichloride") were introduced slowly into 40 ml of a 25% strength ethylamine solution at room temperature, while stirring vigorously. The product which precipitated was filtered off and dried. 8.7 g of dichloromaleic acid bis-ethylamide of melting point 154°–155° C. were obtained. The yield was 81% of theory.

EXAMPLE 2

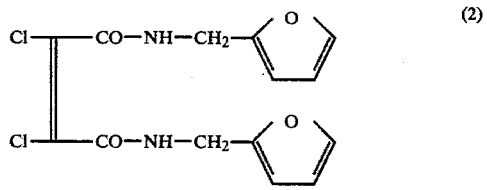

22.2 g (0.1 mol) of dichloromaleic acid dichloride were introduced slowly into a mixture of 20.2 g (0.2 mol) of triethylamine and 19.4 g (0.2 mol) of furfurylamine in 200 ml of acetone at room temperature, while stirring vigorously. The reaction mixture was poured into 100 ml of water and the product which precipitated was filtered off and dried. 29.0 g of dichloromaleic acid bis-furfurylamide of melting point 149° C. were obtained. The yield was 85% of theory.

EXAMPLE 3

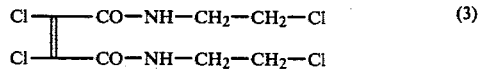

160 g of 10% strength sodium hydroxide solution were added to 40.1 g (0.4 mol) of 2-chloroethylamine hydrochloride, dissolved in 150 ml of water, and 22.2 g (0.1 mol) of dichloromaleic acid dichloride were then introduced slowly at room temperature. The product which precipitated was filtered off and dried. 19.7 g of dichloromaleic acid bis-(2-(chloroethyl)-amide of melting point 107°–110° C. were obtained, that is to say 64% of theory.

The compounds of the general formula

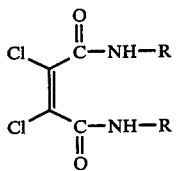

in which R has the meanings given below were prepared analogously to the above examples.

| Compound No. | R | Melting point (°C.) |
|---|---|---|
| 4 | —CH₃ | 162–163 |
| 5 | —C₃H₇(n) | 135–137 |
| 6 | —C₄H₉(n) | 130–132 |
| 7 | —C₄H₉(i) | 166–167 |
| 8 | —CH₂—CH=CH₂ | 127 |
| 9 | —CH₂CH₂CH₂OCH₃ | 83–85 |
| 10 | —CH₂CH₂—N(CH₃)—C₆H₅ | 113–116 |
| 11 | —CH₂—(tetrahydropyran-2-yl) | 139–140 |
| 12 | —CH₂—(3,4-dihydro-2H-pyran-2-yl) | 133–134 |
| 13 | —C₆H₄—F | 187–190 |
| 14 | —C₆H₄—Cl | 185 |
| 15 | —C₆H₄—CF₃ | 147–149 |
| 16 | —C₆H₄—SCF₃ | 138–140 |
| 17 | —C₆H₄—OCF₃ | 146 |
| 18 | —C₆H₄—Cl | 178 |
| 19 | —CH₂—C(CH₃)=CH₂ | 124–125 |
| 20 | —CH₂—C≡CH | 124–126 |

The fungicidal activity of the compounds of this invention is illustrated by the following examples, wherein the compounds according to the present invention are each identified by the number (given in brackets) from the preparative examples hereinabove.

EXAMPLE 4

Mycelium growth test

Nutrient medium used:
20 parts by weight of agar-agar
200 parts by weight of potato decoction
5 parts by weight of malt
15 parts by weight of dextrose
5 parts by weight of peptone
2 parts by weight of disodium hydrogen phosphate
0.3 parts by weight of calcium nitrate
Composition of the solvent mixture:
0.19 part by weight of dimethylformamide
0.01 part by weight of emulsifier (alkylaryl polyglycol ether)
1.80 parts by weight of water
Ratio of solvent mixture to nutrient medium:
2 parts by weight of solvent mixture
100 parts by weight of agar nutrient medium The amount of active compound required for the desired active compound concentration in the nutrient medium was mixed with the stated amount of solvent mixture. The concentrate was thoroughly mixed, in the stated proportion, with the liquid nutrient medium (which had been cooled to 42 deg.C.) and was then poured into Petri dishes of 9 cm diameter. Control plates to which the preparation had not been added were also set up.

When the nutrient medium had cooled and solidified, the plates were inoculated with the species of fungi indicated below and incubated at about 21° C.

Evaluation was carried out after 4–10 days, dependent upon the speed of growth of the organisms. When evaluation was carried out the radial growth of the organism on the treated nutrient media was compared with the growth on the control nutrient medium.

Evaluation of the test showed that, for example, the compounds (1), (6), (7), (15), (14), (2), (3), (8) and (11) had an action against the species of fungi *Sclerotinia sclerotiorum, Fusarium nivale, Collatotrichum coffeanum, Rhizoctonia solani, Verticillium alboatrum, Pyricularia oryzea, Helminthosporium gramineum, Mycoaphaerella musicola, Phytophthora cactorum* and *Pellicularia sasakii* superior to that of the compounds known from the prior art.

EXAMPLE 5

Pyricularia test/liquid preparation of active compound Solvent: 11.75 parts by weight of acetone
  Dispersing agent: 0.75 part by weight of alkylaryl polyglycol ether
  Water: 987.50 parts by weight The amount of active compound required for the desired concentration of active compound in the watering liquid was mixed with the stated amount of the solvent and dispersing agent and the concentrate was diluted with the stated amount of water.

Rice plants about 14 days old were sprayed with the spray liquid until dripping wet. The plants remained in a greenhouse at temperatures of 22° to 24° C. and a relative atmospheric humidity of about 70% until they were dry. They were then inoculated with an aqueous suspension of 100,000 to 200,000 spores/ml of *Pyricularia oryzae* and set up in a chamber at 24° to 26° C. and 100% relative atmospheric humidity.

5 days after the inoculation, the infection of all the leaves present at the time of inoculation was determined as a percentage of the untreated, but also inoculated, control plants.

The evaluation showed that, for example, the compounds (1), (6), (7), (15), (14), (18), (2), (3), (8) and (11)

had a superior action to that of the compounds known from the prior art.

EXAMPLE 6

Phytophthora test (tomato/protective

Solvent: 4.7 parts by weight of acetone
Emulsifier: 0.3 part by weight of alkylaryl polyglycol ether
Water: 95 parts by weight The amount of the active compound required for the desired concentration of the active compound in the spray liquid was mixed with the stated amount of solvent and the concentrate was diluted with the stated amount of water which contained the stated additions.

Young tomato plants with 2 to 4 foliage leaves were sprayed with the spray liquid until dripping wet. The plants remained in a greenhouse for 24 hours at 20 deg.C. and at a relative atmospheric humidity of 70%. The tomato plants were then inoculated with an aqueous spore suspension of *Phytophthora infestans.* The plants were brought into a moist chamber with an atmospheric humidity of 100% and a temperature of 18–20 deg.C.

After 5 days the infection of the tomato plants was determined. Evaluation of the test showed that, for example, the compounds (6), (15), (2), (10), (8), (16), (17) and (11) had a superior action to that of the compounds known from the prior art.

It will be appreciated that the instant specification and examples are set forth by way of illustration and not limitation, and that various modifications and changes may be made without departing from the spirit and scope of the present invention.

What is claimed is:

1. A dichloromaleic acid diamide of the formula

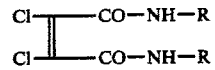

in which
R is an aliphatic radical with up to 6 carbon atoms carrying a heterocyclic group which contains 5 or 6 ring members and an oxygen hetero-atom.

2. A compound according to claim 1, wherein such compound is dichloromaleic acid bis-furfurylamide of the formula

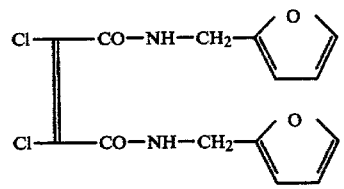

3. A fungicidal composition containing as active ingredient a fungicidally effective amount of a compound according to claim 1 in admixture with a diluent.

4. A method of combating fungi which comprises applying to the fungi, or to a habitat thereof, a fungicidally effective amount of a compound according to claim 1.

5. A method according to claim 4, in which the compound is dichloromaleic acid bis-furfurylamide.

* * * * *